(12) United States Patent
Laich et al.

(10) Patent No.: US 8,784,887 B2
(45) Date of Patent: Jul. 22, 2014

(54) PHARMACEUTICAL PREPARATION OF N-[5-(AMINOSULFONYL)-4-METHYL-1,3-THIAZOL-2-YL]-N-METHYL-2-[4-(2-PYRIDINYL)PHENYL]ACETAMIDE

(75) Inventors: Tobias Laich, Cologne (DE); Katrin Liebelt, Freiburg (DE)

(73) Assignee: Aicuris GmbH & Co. KG, Wuppertal (DE)

( * ) Notice: Subject to any disclaimer, the term of this patent is extended or adjusted under 35 U.S.C. 154(b) by 1215 days.

(21) Appl. No.: 11/904,712

(22) Filed: Sep. 27, 2007

(65) Prior Publication Data
US 2008/0220059 A1    Sep. 11, 2008

Related U.S. Application Data

(63) Continuation of application No. PCT/EP2006/002566, filed on Mar. 21, 2006.

(30) Foreign Application Priority Data

Mar. 30, 2005   (DE) .......................... 10 2005 014 248

(51) Int. Cl.
*A61K 9/20* (2006.01)
*A61K 31/44* (2006.01)

(52) U.S. Cl.
USPC .......................................... 424/465; 514/342

(58) Field of Classification Search
USPC .......................................... 424/465; 514/342
See application file for complete search history.

(56) References Cited

U.S. PATENT DOCUMENTS

| | | | |
|---|---|---|---|
| 3,658,830 A | 4/1972 | Pilgram et al. | |
| 3,717,651 A | 2/1973 | Pilgram et al. | |
| 3,847,588 A | 11/1974 | Pilgram et al. | |
| 4,556,560 A | 12/1985 | Buckingham | |
| 4,762,715 A | 8/1988 | Lukas et al. | |
| 5,034,382 A | 7/1991 | Osswald | |
| 6,328,994 B1 * | 12/2001 | Shimizu et al. | 424/489 |
| 7,105,553 B2 | 9/2006 | Fischer et al. | |
| 2004/0006076 A1 * | 1/2004 | Fischer et al. | 514/227.8 |
| 2004/0235917 A1 | 11/2004 | Betz et al. | |

FOREIGN PATENT DOCUMENTS

| | | |
|---|---|---|
| CA | 2 514 733 | 9/2004 |
| DE | 101 29 716 | 1/2003 |
| DE | 101 31 128 | 1/2003 |
| EP | 0 860 700 | 8/1998 |
| GB | 1323045 | 7/1973 |
| GB | 2311068 | 9/1997 |
| GB | 2311069 | 9/1997 |
| WO | WO-97/24343 | 7/1997 |
| WO | WO-97/36006 | 10/1997 |

(Continued)

OTHER PUBLICATIONS

West, Anthony R. Solid state chemistry and its applications, Wiley, New York, 1988, pp. 358 and 365.*

(Continued)

*Primary Examiner* — Aradhana Sasan
(74) *Attorney, Agent, or Firm* — Morrison & Foerster LLP

(57) ABSTRACT

The invention relates to a pharmaceutical preparation for oral administration comprising N-[5-(aminosulfonyl)-4-methyl-1,3-thiazol-2-yl]-N-methyl-2-[4-(2-pyridinyl)phenyl]acetamide or its hydrates and/or solvates, as well as an acid, a method for its production as well as the use of this preparation for the treatment and/or prophylaxis of diseases which are caused by herpes viruses, in particular diseases which are caused by herpes simplex viruses.

17 Claims, 2 Drawing Sheets

(56) References Cited

FOREIGN PATENT DOCUMENTS

| WO | WO-99/37291 | 7/1999 |
|---|---|---|
| WO | WO-99/42455 | 8/1999 |
| WO | WO-99/47507 | 9/1999 |
| WO | WO-00/53591 | 9/2000 |
| WO | WO-01/47904 | 7/2001 |
| WO | WO-01/96874 | 12/2001 |
| WO | WO-2004/078163 | 9/2004 |

OTHER PUBLICATIONS

Vippagunta et al., Crystalline solids, Advanced Drug Delivery Reviews, 48 (2001) 3-26.*
Crumpacker, Clyde S. Use of antiviral drugs to prevent herpesvirus transmission, New England Journal of Medicine, Jan. 1, 2004, 350:1, pp. 67-68.*
Berge et al., Pharmaceutical Salts, Journal of Pharmaceutical Sciences, vol. 66, No. 1, Jan. 1977, pp. 1-19.*
German Patent Application No. DE 101 29 716, filed on Jun. 22, 2001 (English Abstract Only).
German Patent Application No. DE 101 31 128, filed on Jun. 28, 2001 (English Abstract Only).
Translation of International Preliminary Report on Patentability for PCT/EP2006/002566, issued Oct. 3, 2007, 6 pages.
Crute et al., J. Med. Chem. (1995) 38(10):1820-1825.
Matthews et al., Antiviral Research (1993) 20:89-114.
Artico et al., Eur. J. Med. Chem. (1992) 27:219-228.
Bartmann et al., J. Fluorine Chem. (1993) 61:117-122.
Ziegler and Spragus, J. Org. Chem., Am. Chem. Soc. (1960) 25:1454-1455.
The Merck Manual, 15$^{th}$ ed. (1987) pp. 180-181.
Kleymann et al., Nature Medicine (2002) 8(4):392-398.
Non-Final Office Action from U.S. Appl. No. 10/481,680, mailed on Sep. 21, 2007.
Amendment in Response to Non-Final Office Action from U.S. Appl. No. 10/481,680, filed Jan. 18, 2008.
Final Office Action from U.S. Appl. No. 10/481,680, mailed on Apr. 14, 2008.
Amendment After Final Action and Request for Continued Examination from U.S. Appl. No. 10/481,860, filed Oct. 14, 2008.
Non-Final Office Action from U.S. Appl. No. 10/481,860, mailed on Jan. 16, 2009.
Amendment in Response to Non-Final Office Action from U.S. Appl. No. 10/481,680, filed Apr. 14, 2009.
Final Office Action from U.S. Appl. No. 10/481,860, mailed on Jul. 6, 2009.
Notice of Allowance from U.S. Appl. No. 10/168,197, mailed on Jul. 11, 2003.
Request for Continued Examination from U.S. Appl. No. 10/168,197, filed Oct. 16, 2003.
Non-Final Office Action from U.S. Appl. No. 10/168,197, mailed on Jan. 26, 2004.
Amendment from U.S. Appl. No. 10/168,197, filed Apr. 29, 2004.
Notice of Allowance from U.S. Appl. No. 10/168,197, mailed on Jul. 9, 2004.

* cited by examiner

PHARMACEUTICAL PREPARATION OF N-[5-(AMINOSULFONYL)-4-METHYL-1,3-THIAZOL-2-YL]-N-METHYL-2-[4-(2-PYRIDINYL)PHENYL]ACETAMIDE

CROSS REFERENCE TO RELATED APPLICATIONS

This application is a continuation of pending international application PCT/EP2006/002566, filed Mar. 21, 2006, designating US, which claims priority from German patent application DE 10 2005 014 248.6, filed Mar. 30, 2005. The contents of the above-referenced applications are incorporated herein by this reference in their entirety.

BACKGROUND OF THE INVENTION

The present invention relates to a pharmaceutical preparation for oral application comprising N-[5-(aminosulfonyl)-4-methyl-1,3-thiazol-2-yl]-N-methyl-2-[4-(2-pyridinyl)phenyl]acetamide or its hydrates and/or solvates as well as an acid, a method for its production as well as the use of this preparation for the treatment and/or prophylaxis of diseases which are caused by herpes viruses, in particular diseases which are caused by herpes simplex viruses.

N-[5-(Aminosulfonyl)-4-methyl-1,3-thiazol-2-yl]-N-methyl-2-[4-(2-pyridinyl)phenyl]acetamide is a compound of the following formula which is highly active against diseases which are caused by herpes simplex viruses.

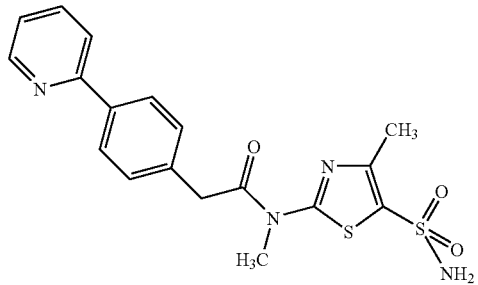 [SMILES: Cc1nc(N(C)C(=O)Cc2ccc(-c3ccccn3)cc2)sc1S(N)(=O)=O]

N-[5-(Aminosulfonyl)-4-methyl-1,3-thiazol-2-yl]-N-methyl-2-[4-(2-pyridinyl)phenyl]acetamide It was first described in WO 01/47904, the disclosure of which is included hereby by reference. When in the following reference is made to active compound (I) all modifications of N-[5-(aminosulfonyl)-4-methyl-1,3-thiazol-2-yl]-N-methyl-2-[4-(2-pyridinyl)phenyl]acetamide as well as the hydrates and/or solvates are included.

For the active compound (I) fast releasing and storage stable tablets are needed for the therapy of herpes diseases in humans. Fast releasing means here that at least 80% of the amount of the active compound are released within 30 minutes in e.g., 0.1 N hydrochloric acid at 37° C. Storage stability is characterized by unchanged release characteristics of the active compound (I) after a storage of the tablet for several weeks or months respectively under defined climate conditions (temperature, humidity) and by the chemical stability of the active compound.

For this the active compound is usually mixed with usual pharmaceutical excipients, possibly granulated and subsequently compressed into tablets. Typical classes of excipients are disintegrants (disintegration auxiliaries), fillers, binders, lubricants and tensides. These can be used on their own or in any combination in order to obtain the desired fast release of the active compound and the storage stability of the preparation (tablet).

If those preparations known from the state of the art are applied to the active compound (I) described here, it has unexpectedly been shown that there is no immediate release of the active compound but that there is a markedly delayed release which is therapeutically not desired.

The cause for this release behavior is a "clumping" or a gel formation respectively of the active compound (I) which is shown in an extreme way in release experiments using pure active compound (I) but which may be assumed to be the cause in the release from tablets as well.

The addition of acidic excipients (acid components) to pharmaceutical preparations in particularly tablets is known in principle. Citric acid for example is often used as a stabilizer (complex formation, change of the pH-value) or as a disintegration auxiliary in effervescent tablets. Other acids such as sorbic acid, propionic acid or benzoic acid are common as preservatives but are not usually found in tablets. Some acids such as for example stearic acid are suitable as lubricant or emulsifiers. Furthermore there are polymeric acids such as polyacrylic acid or polylactides which can also be used as pharmaceutical excipients.

Not described so far is the use of acids without the addition of gas generating substances such as sodium carbonate for the acceleration of the release of the active compound in combination with an improvement of the stability.

One object of the invention was to provide a pharmaceutical formulation from which tablets with sufficient speed of release of the active compound (I) can be produced and which at the same time have excellent storage stability.

SUMMARY OF THE INVENTION

It has surprisingly been found that the object described above can be achieved by a pharmaceutical formulation which comprises in addition to the usual pharmaceutical excipients an acid in a specific quantitative proportion. The addition of gas generating substances is not necessary.

The addition of the acid takes place during the production of the pharmaceutical preparation. Good speeds of release of the active compound (I) from the tablet are achieved particularly well with a combined wet granulation of the active compound (I) with the acid.

Furthermore it has surprisingly been found that the speed of release of the active compound (I) and the storage stability depend on the acid used and on the quantitative proportion of the acid.

The present invention therefore relates to pharmaceutical preparations for oral application comprising N-[5-(aminosulfonyl)-4-methyl-1,3-thiazol-2-yl]-N-methyl-2-[4-(2-pyridinyl)phenyl]acetamide or its hydrates and/or solvates, one or more usual pharmaceutical excipients and an acid whereby the acetamide and the acid form a salt.

Suitable acids are for example hydrochloric acid, acetic acid, sulfuric acid, lactic acid, citric acid, methanesulfonic acid or benzoic acid, with sulfuric acid, methanesulfonic acid or benzoic acid being preferred and methanesulfonic acid or benzoic acid being particularly preferred.

The invention further relates to the salts of N-[5-(aminosulfonyl)-4-methyl-1,3-thiazol-2-yl]-N-methyl-2-[4-(2-pyridinyl)phenyl]acetamide.

Salts of N-[5-(aminosulfonyl)-4-methyl-1,3-thiazol-2-yl]-N-methyl-2-[4-(2-pyridinyl)phenyl]acetamide include for example acid addition salts such as salts of hydrochloric acid, acetic acid, sulfuric acid, lactic acid, citric acid, methanesulfonic acid or benzoic acid and/or hydrates or solvates respectively thereof. Particularly preferred are N-[5-(aminosulfonyl)-4-methyl-1,3-thiazol-2-yl]-N-methyl-[4-(2-pyridinyl)phenyl]acetamide hydrochloride, N-[5-(aminosulfonyl)-4-methyl-1,3-thiazol-2-yl]-N-methyl-2-[4-(2-pyridinyl) phenyl]acetamide mesylate or N-[5-(aminosulfonyl)-4-methyl-1,3-thiazol-2-yl]-N-methyl-2-[4-(2-pyridinyl) phenyl]acetamide benzoate or their hydrates.

The pharmaceutical preparation according to the invention is a preparation for oral application.

The invention further relates to a method for the production of the pharmaceutical preparation characterized in that the acid is added during the production of the pharmaceutical preparation; preferably the active compound (I) is mixed with the acid in a combined wet granulation.

The invention further relates to a method for the production of tablets comprising such preparations.

The invention further relates to tablets having a storage stability of one to six years preferably two to five years.

The formulation according to the invention preferably comprises 30 to 90% particularly preferably 50 to 70% N-[5-(aminosulfonyl)-4-methyl-1,3-thiazol-2-yl]-N-methyl-2-[4-(2-pyridinyl)phenyl]acetamide or hydrates and/or solvates thereof (all percentage data are percentages by weight based on the weight of the pharmaceutical preparations).

The pharmaceutical preparation comprises usually 30 to 1200 mg of active compound (I), preferably 50 to 500 mg and particularly preferably 50 to 250 mg based on a single tablet.

As a component essential for the achievement of the object of the invention the pharmaceutical preparation comprises a stoichiometric ratio of active compound (I) to acid of 1 to 0.10 to 1.10, preferably 1 to 0.50 to 1.00 and particularly preferably 1 to 0.90 to 0.98.

The pharmaceutical preparation according to the invention optionally comprises one or more dry binders which are for example selected from the group consisting of: microcrystalline cellulose, fiber cellulose, calcium phosphates and mannitol. Preferably according to the invention microcrystalline cellulose is used. This is commercially available for example under the designation Avicel®. The pharmaceutical preparation expediently comprises 1 to 20%, preferably 1 to 10%, particularly preferably 1 to 5% of the dry binder(s).

The pharmaceutical preparation according to the invention comprises at least one disintegration auxiliary which is for example selected from the group consisting of starch, pregelatinized starch, starch glycolates, cross-linked polyvinylpyrrolidone, sodium carboxymethylcellulose (=croscarmellose sodium) and other salts of carboxymethylcellulose. A mixture of two disintegration agents can also be used. According to the invention the use of croscarmellose sodium and cross-linked polyvinylpyrrolidone or a mixture of the two is preferred. The pharmaceutical preparation expediently comprises 3 to 35%, preferably 10 to 30% and particularly preferably 15 to 29% of the disintegration auxiliary(ies).

The pharmaceutical preparation of the invention comprises at least one lubricant selected from the group consisting of fatty acids and their salts. According to the invention the use of magnesium stearate is particularly preferred. The lubricant is expediently used in an amount of 0.1 to 2.0%, particularly preferable 0.2 to 1.5% and most preferably 0.5 to 1.1%.

The pharmaceutical preparation of the invention optionally comprises a wetting agent which is selected from the group consisting of the tensides and their salts. According to the invention the use of Tween 80 is particularly preferred. The wetting agent is expediently used in an amount of 0.3 to 2.0%, particularly preferably from 0.4 to 1.5% and most preferably from 0.4 to 0.5%.

A particularly preferred pharmaceutical preparation of the invention comprises:

50 to 70% N-[5-(aminosulfonyl)-4-methyl-1,3-thiazol-2-yl]-N-methyl-2-[4-(2-pyridinyl)phenyl]acetamide or hydrates and/or solvates thereof, 15 to 29% croscarmellose-sodium and cross-linked polyvinylpyrrolidon (4:1), 0.5 to 1.1% magnesium stearate, 1 to 5% microcrystalline cellulose, optionally 0.4 to 0.5% Tween 80, as well as of methanesulfonic acid with a stoichiometric ratio of acetamide to acid of 1 to 0.90 to 0.98 whereby the acetamide and the acid form a salt.

The pharmaceutical preparation of the invention can expediently be produced by a method in which N-[5-(aminosulfonyl)-4-methyl-1,3-thiazol-2-yl]-N-methyl-2-[4-(2-pyridinyl)phenyl]acetamide, its hydrate and/or solvate, optionally one or more dry binders and an acid are subjected to an aqueous granulation, the granules are subsequently mixed with at least one disintegration auxiliary and at least one lubricant and optionally one wetting agent and optionally tabletted and varnished.

For the granulation methods according to the principle of rapid mixing granulation can be used. The granulation can take place with water without the addition of a binder.

The pharmaceutical preparation of the present invention is particularly preferably used in the form of a tablet formulation which can optionally be varnished (as already mentioned above weight data in the present patent application are based on the total weight of the pharmaceutical preparation without the weight of the optionally present varnish). For the varnish varnishing formulations usual in pharmaceutical technology can be used, such as for example those based on hydroxypropylmethylcellulose (HPMC) and/or polyethylenglyocol of various molecular weights. Furthermore the varnish can comprise usual pigments or colors such as for example titanium dioxide or iron oxide.

The pharmaceutical preparation according to the invention is preferably used for the treatment and/or prophylaxis of diseases which are caused by herpes viruses, in particular diseases which are caused by herpes simplex viruses.

DETAILED DESCRIPTION OF PREFERRED EMBODIMENTS

Examples

The production of the tablets takes place on a laboratory scale under comparable granulation and tabletting conditions.

First granules or powder mixtures respectively are produced. These are compressed into tablets with a total weight resulting from the example using usual tablet presses and using a compression tool with the format 6 mm, radius of curvature 9 mm. The breaking strength of the tablet on a usual test instrument (e.g., Schleuniger 6D) should be about 60 N.

Optionally the tablets can be coated with a varnish. For this for example an aqueous 3.5% (weight/weight) suspension (solids: 60% hydroxypropyl methylcellulose with a 15 cp viscosity, 20% polyethylenglycol 400 and 20% pigments such as, e.g., iron oxide and/or titanium dioxide) can be used. The process steps and instruments necessary hereby are well-known to the man of the art. Data on the amounts of varnish in the examples are based on mg varnish solid per tablet, same with the amounts stated in the example recipes (mg solid per tablet).

For the production of 85 g of tablets according to example 1 the amounts are calculated corresponding to the size of the batch and the solids are mixed. Sufficient for mixing are for example 15 min. in a 1 liter mixing vessel in a Turbula mixer (Bachofen; Switzerland). The mixture is compressed into tablets as described and the tablets can optionally be varnished.

For the production of 50 g of granules each of the examples 2 to 8 the components are weighed in corresponding to the batch size in the composition stated. Thereby for examples 2 to 4 42.5 mg of water each per tablet each and for examples 5, 6 and 8 60 mg of water per tablet and for example 780 mg of water per tablet are used for the granulation. The polyvinylpyrrolidone as well as optionally the tensides or the acid components are dissolved in the amount of water. All further components with the exception of the magnesium stearate are granulated with this solution. This takes place in a mortar of appropriate size. The addition of the granulating solution takes place in portions. The wet mass is subsequently pressed through a 2 mm laboratory sieve and dried in a drying oven at 60 to 80° C. The dry granules are mixed with the necessary amount of magnesium stearate (5 min, 1l vessel, Turbula mixer). The mixture is compressed into tablets as described and the tablets can optionally be varnished.

The expression "micronized active compound" refers to crystalline active compound which is micronized. The particle size thereby is 1.04 μm (lower×10), 2.97 μm (middle× 50) and 6.29 μm (upper×90).

Example 1

Comparative Example

Standard tablet comprising 50 mg of N-[5-(aminosulfonyl)-4-methyl-1,3-thiazol-2-yl]-N-methyl-2-[4-(2-pyridinyl)phenyl]acetamide as crystalline active compound, content of active compound about 59% (based on an unvarnished tablet):

| | |
|---|---|
| N-[5-(Aminosulfonyl)-4-methyl-1,3-thiazol-2-yl]-N-methyl-2-[4-(2-pyridinyl)phenyl]acetamide, crystalline | 50.00 mg |
| Microcrystalline cellulose | 10.15 mg |
| Croscarmellose sodium | 24.00 mg |
| Magnesium stearate | 0.85 mg |
| optionally HPMC varnish | 2.70 mg |

Example 2

Tablet comprising 50 mg of N-[5-(aminosulfonyl)-4-methyl-1,3-thiazol-2-yl]-N-methyl-2-[4-(2-pyridinyl)phenyl]acetamide as micronized active compound, content of active compound about 59% (based on an unvarnished tablet) and methanesulfonic acid in a molar ratio of 5%:

| | |
|---|---|
| N-[5-(Aminosulfonyl)-4-methyl-1,3-thiazol-2-yl]-N-methyl-2-[4-(2-pyridinyl)phenyl]acetamide, micronized | 50.00 mg (0.124 mmol) |
| Polyvinylpyrrolidone 25 | 3.50 mg |
| Microcrystalline cellulose | 20.05 mg |
| Methanesulfonic acid | 0.60 mg (0.006 mmol) |
| Croscarmellose sodium | 10.00 mg |
| Magnesium stearate | 0.85 mg |
| optionally HPMC varnish | 3.00 mg |

Example 3

Tablet comprising 50 mg of N-[5-(aminosulfonyl)-4-methyl-1,3-thiazol-2-yl]-N-methyl-2-[4-(2-pyridinyl)phenyl]acetamide as micronized active compound, content of active compound about 59% (based on an unvarnished tablet) and methanesulfonic acid in a molar ratio of 10%:

| | |
|---|---|
| N-[5-(Aminosulfonyl)-4-methyl-1,3-thiazol-2-yl]-N-methyl-2-[4-(2-pyridinyl)phenyl]acetamide, micronized | 50.00 mg (0.124 mmol) |
| Polyvinylpyrrolidone 25 | 3.50 mg |
| Microcrystalline cellulose | 19.46 mg |
| Methanesulfonic acid | 1.19 mg (0.012 mmol) |
| Croscarmellose sodium | 10.00 mg |
| Magnesium stearate | 0.85 mg |
| optionally HPMC varnish | 3.00 mg |

Example 4

Tablet comprising 50 mg of N-[5-(aminosulfonyl)-4-methyl-1,3-thiazol-2-yl]-N-methyl-2-[4-(2-pyridinyl)phenyl]acetamide as micronized active compound, content of active compound about 59% (based on an unvarnished tablet) and methanesulfonic acid in a molar ratio of 50%:

| | |
|---|---|
| N-[5-(Aminosulfonyl)-4-methyl-1,3-thiazol-2-yl]-N-methyl-2-[4-(2-pyridinyl)phenyl]acetamide, micronized | 50.00 mg (0.124 mmol) |
| Polyvinylpyrrolidone 25 | 3.50 mg |
| Microcrystalline cellulose | 14.70 mg |
| Methanesulfonic acid | 5.95 mg (0.062 mmol) |
| Croscarmellose sodium | 10.00 mg |
| Magnesium stearate | 0.85 mg |
| optionally HPMC varnish | 3.00 mg |

Example 5

Tablet comprising 50 mg of N-[5-(aminosulfonyl)-4-methyl-1,3-thiazol-2-yl]-N-methyl-2-[4-(2-pyridinyl)phenyl]acetamide as micronized active compound, content of active compound about 56% (based on an unvarnished tablet) and methanesulfonic acid in a molar ratio of 95%:

| | |
|---|---|
| N-[5-(Aminosulfonyl)-4-methyl-1,3-thiazol-2-yl]-N-methyl-2-[4-(2-pyridinyl)phenyl]acetamide, micronized | 50.00 mg (0.124 mmol) |
| Polyvinylpyrrolidone 25 | 5.00 mg |
| Microcrystalline cellulose | 1.41 mg |
| Methanesulfonic acid | 11.30 mg (0.118 mmol) |
| Croscarmellose sodium | 20.00 mg |
| Magnesium stearate | 0.89 mg |
| Tween 80 | 0.40 mg |
| optionally HPMC varnish | 3.00 mg |

Example 6

Tablet comprising 50 mg of N-[5-(aminosulfonyl)-4-methyl-1,3-thiazol-2-yl]-N-methyl-2-[4-(2-pyridinyl)phenyl]acetamide as micronized active compound, content of active compound about 60% (based on an unvarnished tablet) and sulfuric acid (95%) in a molar ratio of 47% (two-proton acid, i.e., effectively 94%):

| | |
|---|---|
| N-[5-(Aminosulfonyl)-4-methyl-1,3-thiazol-2-yl]-N-methyl-2-[4-(2-pyridinyl)phenyl]acetamide, micronized | 50.00 mg (0.124 mmol) |
| Polyvinylpyrrolidone 25 | 5.00 mg |
| Microcrystalline cellulose | 1.75 mg |
| Sulfuric acid (95%) | 6.00 mg (0.058 mmol) |
| Croscarmellose-sodium | 20.00 mg |
| Magnesium stearate | 0.85 mg |
| Tween 80 | 0.40 mg |
| optionally HPMC varnish | 3.00 mg |

Example 7

Tablet comprising 50 mg of N-[5-(aminosulfonyl)-4-methyl-1,3-thiazol-2-yl]-N-methyl-2-[4-(2-pyridinyl)phenyl]acetamide as micronized active compound, content of active compound about 57% (based on an unvarnished tablet) and lactic acid (90%) in a molar ratio of 94%:

| | |
|---|---|
| N-[5-(Aminosulfonyl)-4-methyl-1,3-thiazol-2-yl]-N-methyl-2-[4(2-pyridinyl)phenyl]acetamide, micronized | 50.00 mg (0.124 mmol) |
| Polyvinylpyrrolidone 25 | 5.00 mg |
| Microcrystalline cellulose | 0.00 mg |
| Lactic acid (90%) | 11.70 mg (0.117 mmol) |
| Croscarmellose sodium | 20.00 mg |
| Magnesium stearate | 0.90 mg |
| Tween 80 | 0.40 mg |
| optionally HPMC varnish | 3.00 mg |

Example 8

Tablet comprising 50 mg of N-[5-(aminosulfonyl)-4-methyl-1,3-thiazol-2-yl]-N-methyl-2-[4-(2-pyridinyl)phenyl]acetamide as micronized active compound, content of active compound about 54% (based on an unvarnished tablet) and benzoic acid in a molar ratio of 100%:

| | |
|---|---|
| N-[5-(Aminosulfonyl)-4-methyl-1,3-thiazol-2-yl]-N-methyl-2-[4(2-pyridinyl)phenyl]acetamide, micronized | 50.00 mg (0.124 mmol) |
| Polyvinylpyrrolidone 25 | 5.00 mg |
| Microcrystalline cellulose | 1.47 mg |
| Benzoic acid | 15.20 mg (0.124 mmol) |
| Croscarmellose sodium | 20.00 mg |
| Magnesium stearate | 0.93 mg |
| Tween 80 | 0.40 mg |
| optionally HPMC varnish | 3.00 mg |

In order to determine the storage stability of the tablets they are stored as generally usual in open glass vessels at the stated temperatures or humidities respectively. After certain times the chemical and physical stability of the tablet is tested. This method is generally usual in the industrial development of tablets for use as medicaments and known to a man of the art.

| Time [min] | Sulfuric Acid Release [%] | Lactic Acid Release [%] | Benzoic Acid Release [%] | Methane-sulfonic Acid Release [%] | Standard Tablet Release [%] |
|---|---|---|---|---|---|
| 0 | 0 | 0 | 0 | 0 | 0 |
| 5 | 84 | 49 | 94 | 63 | 6 |
| 10 | 93 | 86 | 94 | 82 | 10 |
| 15 | 94 | 99 | 94 | 86 | 13 |
| 20 | 95 | 99 | 95 | 88 | 16 |
| 25 | 95 | 99 | 95 | 89 | 19 |
| 30 | 95 | 99 | 95 | 90 | 21 |
| 45 | 95 | 99 | 95 | 92 | 28 |
| 60 | 96 | 99 | 95 | 93 | 34 |

Figure 1:
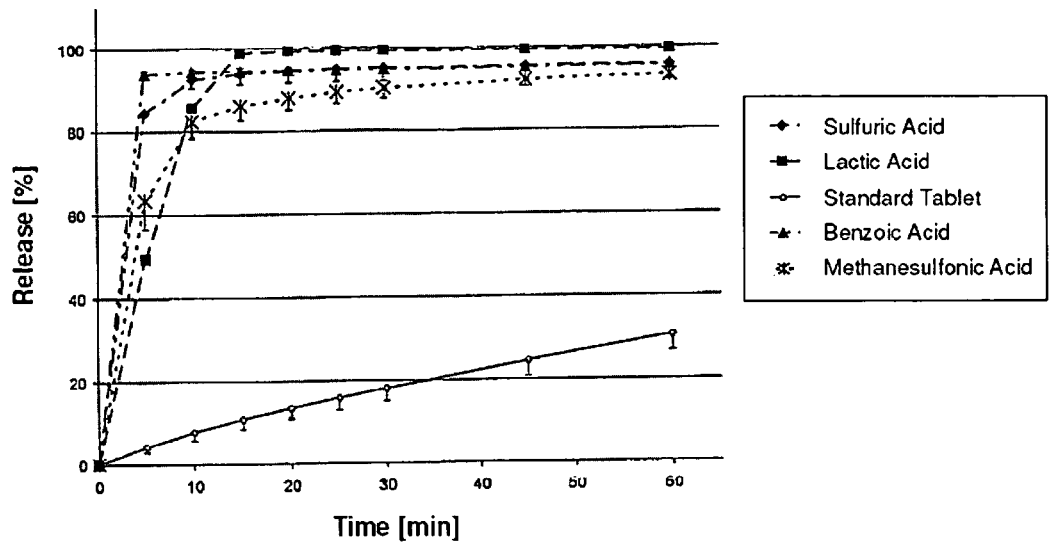
FIG. 1 shows the comparison of the release of N-[5-(aminosulfonyl)-4-methyl-1,3-thiazol-2-yl]-N-methyl-2-[4-2-pyridinyl)phenyl]acetamide from standard tablets and tablets with the addition of acid in 0.1 N hydrochloric acid at 37° C.

FIG. 1 clearly shows the improved release of N-[5-(aminosulfonyl)-4-methyl-1,3-thiazol-2-yl]-N-methyl-2-[4-(2-pyridinyl)phenyl]acetamide from tablets with the addition of acid.

Figure 2:
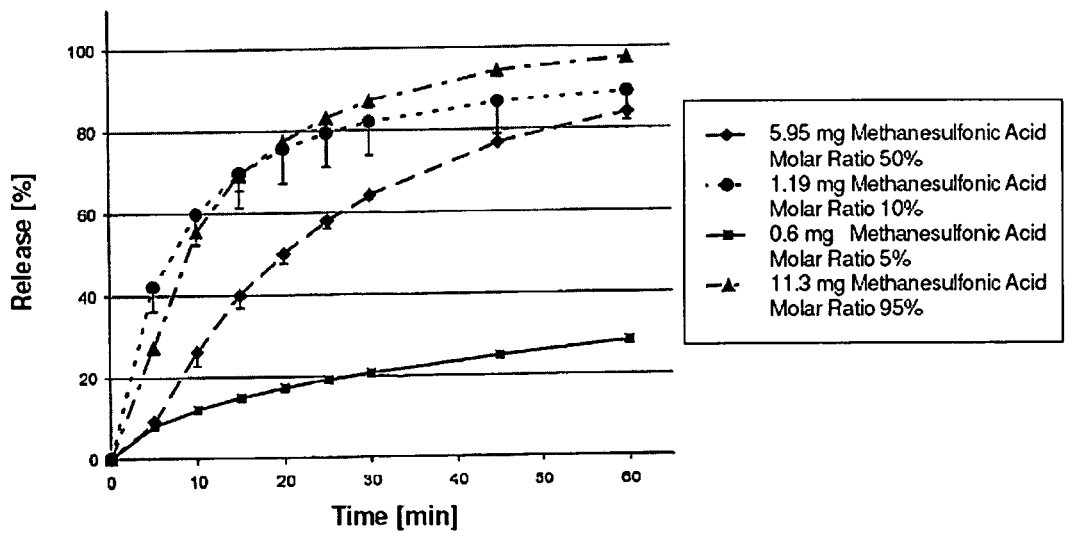

FIG. 2 shows the comparison of the release of N-[5-(aminosulfonyl)-4-methyl-1,3-thiazol-2-yl]-N-methyl-2-[4-(2-pyridinyl)phenyl]acetamide from tablets with different molar amounts of methanesulfonic acid in 0.1 N hydrochloric acid at 37° C.

| Time [min] | 5% Methanesulfonic Acid Release [%] | 10% Methanesulfonic Acid Release [%] | 50% Methanesulfonic Acid Release [%] | 95% Methanesulfonic Acid Release [%] |
|---|---|---|---|---|
| 0 | 0 | 0 | 0 | 0 |
| 5 | 8 | 42 | 9 | 27 |
| 10 | 12 | 60 | 26 | 56 |
| 15 | 15 | 70 | 40 | 69 |
| 20 | 17 | 76 | 50 | 77 |
| 25 | 19 | 79 | 58 | 83 |
| 30 | 21 | 82 | 64 | 87 |
| 45 | 25 | 87 | 77 | 94 |
| 60 | 28 | 89 | 84 | 97 |

FIG. 2 clearly shows the improved release of N-[5-(aminosulfonyl)-4-methyl-1,3-thiazol-2-yl]-N-methyl-2-[4-(2-pyridinyl)phenyl]acetamide from tablets with a high molar proportion of methanesulfonic acid.

Figure 3:
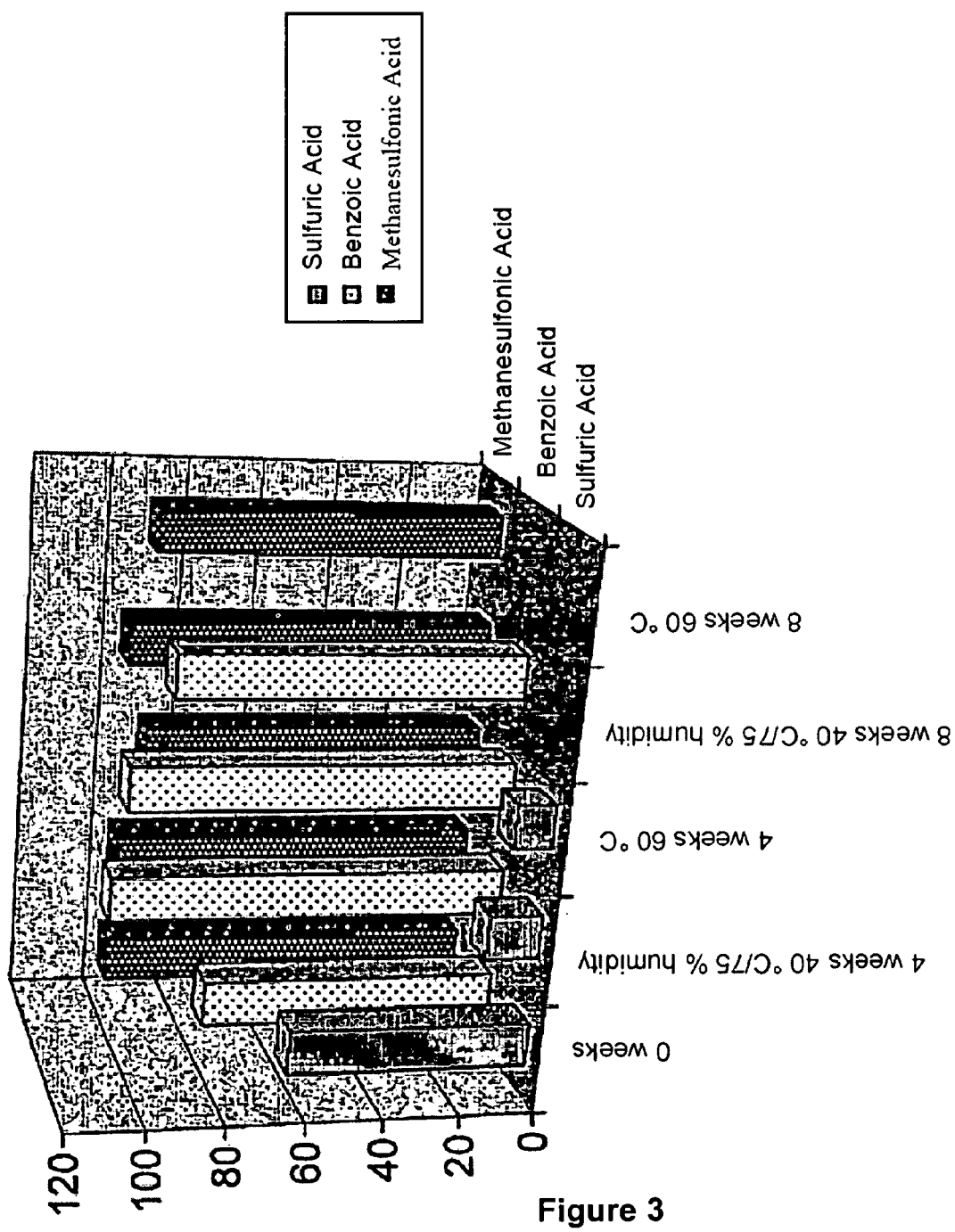

FIG. 3 shows the comparison of the release of N-[5-(aminosulfonyl)-4-methyl-1,3-thiazol-2-yl]-N-methyl-2-[4-(2-pyridinyl)phenyl]acetamide from tablets after 15 min. [%] depending on the time and conditions of storage.

| Acid | 0 Weeks | 4 Weeks 40° C./75% Humidity | 4 Weeks 60° C. | 8 Weeks 40° C./75% Humidity | 8 Weeks 60° C. |
|---|---|---|---|---|---|
| Sulfuric Acid | 63 | 14 | 10 | — | — |
| Benzoic Acid | 78 | 104 | 101 | 91 | — |
| Methane-sulfonic Acid | 98 | 97 | 91 | 97 | 91 |

FIG. 3 clearly shows the improved storage stability of N-[5-(aminosulfonyl)-4-methyl-1,3-thiazol-2-yl]-N-methyl-2-[4-(2-pyridinyl)phenyl]acetamide in tablets with the use of methanesulfonic acid for the production of the pharmaceutical formulation.

What is claimed is:
1. A pharmaceutical preparation for oral application comprising

N-[5-(aminosulfonyl)-4-methyl-1,3-thiazol-2-yl]-N-methyl-2-[4-(2-pyridinyl)phenyl]acetamide or a hydrate thereof,
optionally one or more dry binders,
at least one disintegration auxiliary,
at least one lubricant and
optionally a tenside,
said preparation comprising methanesulfonic acid which is used in a stoichiometric ratio of N-[5-(aminosulfonyl)-4-methyl-1,3-thiazol-2-yl]-N-methyl-2-[4-(2-pyridinyl)phenyl]acetamide or said hydrate to acid of 1 to 0.10 to 1.10 whereby said acetamide and said acid form a salt.

2. The preparation of claim 1, comprising 30 to 1200 mg of N-[5-(aminosulfonyl)-4-methyl-1,3-thiazol-2-yl]-N-methyl-2-[4-(2-pyridinyl)phenyl]acetamide or a hydrate based on a single tablet.

3. The preparation of claim 1, wherein said dry binder is microcrystalline cellulose.

4. The preparation of claim 1, wherein said disintegration auxiliary is croscarmellose sodium or a mixture of croscarmellose sodium and cross-linked polyvinylpyrrolidone (4:1).

5. The preparation of claim 1, wherein said lubricant is magnesium stearate.

6. The preparation of claim 1, wherein said tenside is polysorbate 80.

7. The preparation of claim 1, comprising:
50 to 70% N-[5-(aminosulfonyl)-4-methyl-1,3-thiazol-2-yl]-N-methyl-2-[4-(2-pyridinyl)phenyl]acetamide or hydrates thereof,
15 to 29% croscarmellose sodium and cross-linked polyvinylpyrrolidone (4:1),
0.5 to 1.1% magnesium stearate,
1 to 5% microcrystalline cellulose,
optionally 0.4 to 0.5% polysorbate 80, as well as
methanesulfonic acid with a stoichiometric ratio of acetamide to acid of 1 to 0.90 to 0.98 whereby said acetamide and said acid form a salt.

8. A tablet preparation for oral application comprising a core of said pharmaceutical preparation of claim 1 and a varnish coating.

9. The preparation of claim 1, comprising N-[5-(aminosulfonyl)-4-methyl-1,3-thiazol-2-yl]-N-methyl-2-[4-(2-pyridinyl)phenyl]acetamide.

10. The preparation of claim 8, comprising N-[5-(aminosulfonyl)-4-methyl-1,3-thiazol-2-yl]-N-methyl-2-[4-(2-pyridinyl)phenyl]acetamide.

11. The preparation of claim 1 for the treatment of diseases which are caused by herpes viruses, in particular diseases which are caused by herpes simplex viruses.

12. The preparation of claim 8 for the treatment of diseases which are caused by herpes viruses, in particular diseases which are caused by herpes simplex viruses.

13. A method for the production of the pharmaceutical preparation for oral application of claim 1, wherein N-[5-(Aminosulfonyl)-4-methyl-1,3-thiazol-2-yl]-N-methyl-2-[4-(2-pyridinyl)phenyl]acetamide or a hydrate thereof, optionally one or more dry binders and an acid are subjected to an aqueous granulation to form granules, said granules are subsequently mixed with at least one disintegration auxiliary and at least one lubricant and optionally a wetting agent and optionally tabletted and varnished.

14. A method for the production of the pharmaceutical preparation for oral application of claim 8, wherein N-[5-(Aminosulfonyl)-4-methyl-1,3-thiazol-2-yl]-N-methyl-2-[4-(2-pyridinyl)phenyl]acetamide or a hydrate thereof, optionally one or more dry binders and an acid are subjected to an aqueous granulation to form granules, said granules are subsequently mixed with at least one disintegration auxiliary and at least one lubricant and optionally a wetting agent and optionally tabletted and varnished.

15. A compound selected from the group consisting of:
N-[5-(Aminosulfonyl)-4-methyl-1,3-thiazol-2-yl]-N-methyl-2-[4-(2-pyridinyl)phenyl]acetamide mesylate, and its hydrates.

16. The preparation of claim 1, wherein, when treated with 0.1 N HCl at 37° C., the preparation releases said acetamide faster than a preparation lacking methanesulfonic acid releases said acetamide.

17. The preparation of claim 1, wherein at least 80% of said acetamide is released from the preparation within 30 minutes in 0.1 N HCl at 37° C.

* * * * *